United States Patent [19]

Onuki et al.

[11] Patent Number: 4,658,055

[45] Date of Patent: Apr. 14, 1987

[54] METHOD FOR MANUFACTURE OF 7-(2,5-DIOXOCYCLOPENTYL)HEPTANOIC ACID DERIVATIVE

[75] Inventors: Takashi Onuki; Hirokazu Naora, both of Kawasaki; Asao Nakamura, Tokyo, all of Japan

[73] Assignee: Ajinomoto Co., Inc., Tokyo, Japan

[21] Appl. No.: 695,187

[22] Filed: Jan. 28, 1985

[30] Foreign Application Priority Data

Jan. 27, 1984 [JP] Japan ................................. 59-12875
Jun. 19, 1984 [JP] Japan ................................. 59-126259

[51] Int. Cl.$^4$ ............................................. C07C 67/28
[52] U.S. Cl. .................................... 562/503; 560/231
[58] Field of Search ................. 562/503; 560/106, 231

[56] References Cited

U.S. PATENT DOCUMENTS 3,900,512  8/1975  Sih .................................. 562/503 X
4,281,153  7/1981  Floyd, Jr. et al. ............. 562/503 X
4,321,405  3/1982  Weiss .............................. 562/503 X

*Primary Examiner*—Natalie Trousof
*Assistant Examiner*—Patricia M. Scott
*Attorney, Agent, or Firm*—Oblon, Fisher, Spivak, McClelland & Maier

[57] ABSTRACT

A method for the manufacture of a heptanoic acid derivative represented by the formula

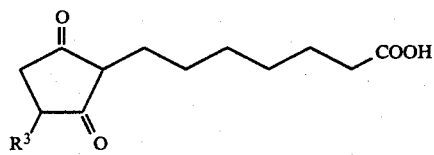

wherein $R^3$ stands for an acyloxy group, a halogen atom, or a hydrogen atom, which comprises reacting a cyclooctene derivative represented by the formula

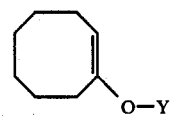

wherein Y stands for $-R^1$, $-COR^1$ or $-SiR^2_3$, wherein $R^1$ is an alkyl group, an aryl group, or an aralkyl group and $R^2$ is an alkyl group of 1 to 5 carbon atoms, with a compound represented by the formula

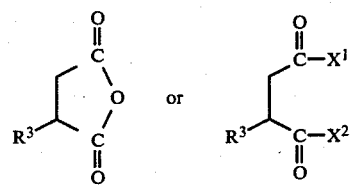

wherein $R^3$ has the same meaning as indicated above and $X^1$ and $X^2$ each is a halogen atom, is described along with uses for such compounds.

4 Claims, No Drawings

METHOD FOR MANUFACTURE OF 7-(2,5-DIOXOCYCLOPENTYL)HEPTANOIC ACID DERIVATIVE

BACKGROUND OF THE INVENTION

1. Field of the Invention

This invention relates to a method for the manufacture of a heptanoic acid derivative useful as an intermediate for the production of prostaglandins.

2. Description of the Prior Art

Prostaglandins possess many pharmacological activities such as the ability to impede coagulation of blood platelets, the ability to lower or elevate blood pressure, the ability to contract smooth muscles, and the ability to suppress excretion of gastric juice. Prostaglandins therefore are useful as medicines for the prevention and cure of various diseases such as thrombosis, hypertension, and peptic ulcer.

Prostaglandins are easily produced from 7-(2,5-dioxocyclopentyl)heptanoic acid (Chem. Pharm. Bull., 17, 408 (1969) and Agr. and Biol. Chem., 33, 1078 (1969), for example, both of which are herein incorporated by reference). The methods heretofore known for the production of 7-(2,5-dioxocyclopentyl)heptanoic acid suffer from the problem that the processes for synthesis involved therein are extremely long [Chem. Pharm. Bull., 17, 408 (1969) and Agr. and Biol. Chem., 33, 1078 (1969)] or the preparation of catalysts used therefor is complicated [Chem. Ber., 113, 2939 (1980)]. This circumstance has resulted in a need for the development of a commercially advantageous method for the manufacture of this acid.

SUMMARY OF THE INVENTION

Accordingly, it is an object of this invention to produce a commercially advantageous method for the manufacture of 7-(2,5-dioxocyclopentyl)heptanoic acid.

This and other objects of the invention as will hereinafter become more readily apparent had been accomplished by providing a method for the manufacture of a heptanoic acid derivative represented by the formula

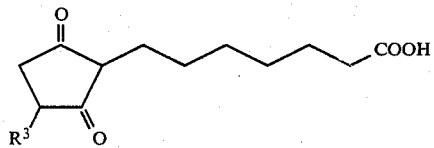

wherein $R^3$ stands for an acyloxy group, a halogen atom, or a hydrogen atom, which comprises:

reacting a cyclooctene derivative represented by the formula

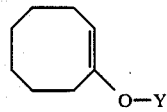

wherein Y stands for $-R^1$, $-COR^1$ or $-SiR^2{}_3$, wherein $R^1$ is an alkyl group, an aryl group, or an aralkyl group and $R^2$ is an alkyl group of 1 to 5 carbon atoms, with a compound represented by the formula

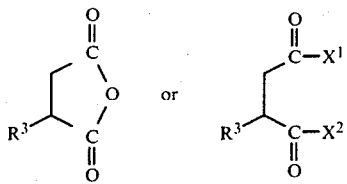

wherein $R^3$ has the same meaning as indicated above and $X^1$ and $X^2$ each is a halogen atom.

DESCRIPTION OF THE PREFERRED EMBODIMENTS

The inventors undertook a diligent study with a view toward developing a method capable of easily and inexpensively producing 7-(2,5-dioxocyclopentyl)heptanoic acid useful for the production of prostaglandins. They have found that 7-(2,5-dioxocyclopentyl)heptanoic acid of high purity is produced very easily and inexpensively by subjecting 1-cyclooctenyl acetate, 1-cyclooctenyloxytriorganosilane or 1-alkoxycyclooctene (and related compounds) and succinic anhydride or succinyl halide to Friedel-Crafts reaction and treating the resultant reaction product with water or an aqueous acid or alkaline solution. They have perfected the present invention based on this knowledge.

Specifically, this invention is characterized by producing a heptanoic acid derivative represented by the formula

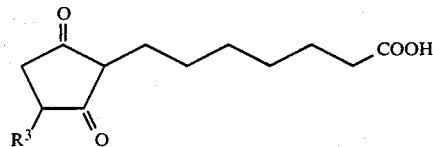

by the reaction a cyclooctene derivative represented by the formula

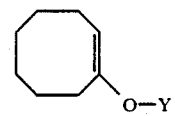

(wherein Y stands for $-R^1$, $-COR^1$ or $-SiR^2{}_3$) with a compound represented by the general formula

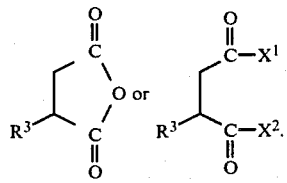

In the foregoing formulas, $R^1$ stands for an alkyl group, an aryl group, or an aralkyl group, $R^2$ for an alkyl group of 1 to 5 carbon atoms, $R^3$ for an acyloxy group such as acetoxy or butyroxy, a halogen atom such as chlorine or bromine, or a hydrogen atom, and $X^1$ and $X^2$ each stands for a halogen atom. Preferred alkyl groups are those containing 1 to 5 carbon atoms. Preferred aryl groups are phenyl groups and phenyl groups substituted by one or more alkyl group. Preferred aralkyl groups are 1- to 5-carbon alkyl groups substituted by a phenyl group, which itself may be substituted by an alkyl group as described immediately above. Particularly preferred alkyl groups include methyl, ethyl, propyl, isopropyl, butyl, isobutyl, and tertiary butyl groups. Particularly preferred aryl groups include phenyl and phenyl substituted by one or more of the preferred alkyl groups, particularly if in the 2, 4, or 6 positions. Especially preferred substituted phenyl groups contain one of the preferred alkyl groups in the 4 position. Particularly preferred aralkyl groups include benzyl and benzyl substituted in the same manner as the preferred aryl groups. Preferred acyloxy groups are alkanoyloxy, aroyloxy, and aralkanoyloxy groups in which the preferred alkyl, aryl, and aralkyl groups are those enumerated above. Preferred halogen atoms for $X^1$ and $X^2$ are chlorine and bromine with $X^1$ and $X^2$ preferably being identical.

As the catalyst, a Lewis acid intended for the Friedel-Crafts reaction is adopted. Examples of the Lewis acid are aluminium chloride, aluminium bromide, tin chloride, boron trifluoride, zinc chloride, and titanium tetrachloride. It is not particularly necessary to use a solvent for the reaction. When a solvent is used at all, it helps to promote the reaction. Examples of the solvent usable for the reaction include methylene chloride, 1,2-dichloroethane, nitromethane, nitrobenzene, 1,1,2-trichloroethane, and 1,1,2,2-tetrachloroethane.

Presence of a halogenated trialkylsilane (having about 1 to 5 carbon atoms in the alkyl group thereof) such as chlorotrimethylsilane in the reaction system proves advantageous because this compound improves the yield.

It has been found that the isolation of 7-(2,5-dioxocyclopentyl)heptanoic acid from the reaction mixture and the refinement of the separated acid are accomplished simply by extraction of the acid into an aqueous alkaline solution. Nonacidic impurities can be readily removed by extracting the alkaline aqueous solution of the acid with an organic solvent. These procedures are entirely conventional and can readily be accomplished by those skilled in the art of organic synthesis. Examples of aqueous alkaline solutions include sodium bicarbonate, sodium carbonate, buffers having a pH of 11 or less, and dilute solutions of strong bases such as sodium hydroxide. Saturated aqueous sodium bicarbonate solution is a preferred extracting agent. Once the product acid is extracted into an aqueous alkaline solution, the solution can be washed with an organic solvent, such as ether or ethyl acetate, to remove impurities. The desired final product can be separated from the water in the aqueous solution by adjusting the pH of the alkaline solution to an acid pH and extracting the resulting protonated form of the acid with an organic solvent such as ethyl acetate. The organic layer is then removed, typically by warming under a vacuum.

Since the method of the invention relies on two reaction steps followed by extremely simple and standard techniques of isolating the final product from the reaction mixture, the method of the invention is an extremely simple and convenient means for producing 7-(2,5-dioxocyclopentyl)heptanoic acid.

In this invention, when 1-cyclooctenyl acetate is selected as the cyclooctene derivative as the starting material, the acetate can be produced very easily in high yield by the reaction of isopropenyl acetate with cyclooctanone in the presence of an acid. When 1-cyclooctenyloxytrimethylsilane is selected as the starting material, the cyclooctene derivative can be prepared by the reaction of chlorotrimethylsilane with cyclooctanone in the presence of an acid. When 1-alkoxycyclooctene is selected as the starting material, the cyclooctene derivative can be produced by the reaction of alkyl orthoformate with cyclooctanone in the presence of an acid. These three specific reactions are examples of those that can be carried out in accomplishing this invention, and many variations thereof will readily produce the same results as will be appreciated by those skilled in the art.

The synthesis of prostaglandins from 7-(2,5-dioxocyclopentyl)heptanoic acid has been disclosed in various articles of literature (such as, for example Agr. and Biol. Chem., 33, 1078 (1969) and Chem. Pharm. Bull., 17, 408 (1969)). Heretofore, this synthesis has entailed a long series of steps (for example, 7 steps starting from diethyl malonate). The conventional methods, therefore, have suffered from practical problems of yield and complexity. The conventional method which uses diethyl malonate as the starting material is as shown below.

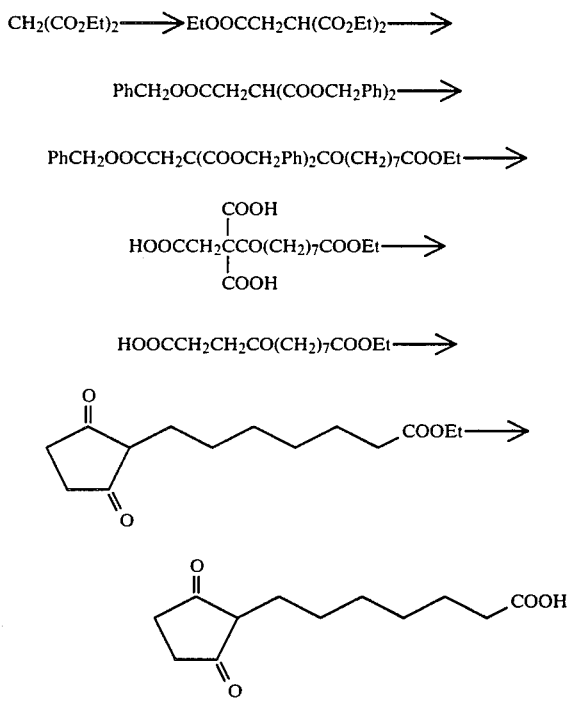

The present invention is highly useful in that is permits a 7-(2,5-dioxocyclopentyl)heptanoic acid derivative to be produced very easily in high yield as described above. The present invention also permits the heptanoic acid derivative to be produced through only two steps. The procedure of the reaction and the isolation and the refinement of the product are extremely simple. Thus, the present invention is decisively improved over the conventional method in terms of production process and equipment.

The invention now being generally described, the same will be better understood by reference to the following examples which are included for purpose of illustration only and are not to be considered limiting of the invention unless otherwise specified.

EXAMPLES

Example 1

In the presence of 0.6 g of para-toluenesulfonic acid, 50 g (0.4 mol) of cyclooctanone and 100 ml (0.9 mol) of isopropenyl acetate were refluxed for 11 hours. The reaction mixture was cooled, stirred with 0.6 g of anhydrous sodium carbonate at room temperature for one hour, left standing overnight, and filtered. The filtrate was distilled under reduced pressure to afford 60 g (91% in yield) of 1-cyclooctenyl acetate having a boiling point of 71° to 73° C./3 mmHg.

In 5 ml of 1,2-dichloroethane, 2.7 g of aluminium chloride was suspended. To the resultant suspension, 1 g (10 mmol) of succinic anhydride was added and then 1.66 g (10 mmol) of 1-cyclooctenyl acetate obtained as described above was added dropwise over a period of about three minutes. The resultant mixture was stirred at room temperature for one hour. This mixture was stirred at 70° C. for five hours, then cooled, poured into 50 ml of 1N hydrochloric acid containing ice, and extracted three times with 30 ml of ethyl acetate. The extract was concentrated, and the residue was stirred with 30 ml of a saturated aqueous sodium bicarbonate solution and 30 ml of ether and separated. The residue was again stirred with 20 ml of a saturated aqueous sodium bicarbonate solution and 20 ml of ether, and separated. The aqueous layers were combined and washed three times with 20 ml of ether. The aqueous layer was adjusted to pH 1-2 with 6N hydrochloric acid and extracted with ethyl acetate. The organic layer was dried and concentrated. The residue was washed twice with 3 ml of water and dried. Consequently, 0.24 g (11% in yield) of 7-(2,5-dioxocyclopentyl)heptanoic acid was obtained. This product had a melting point of 138° to 146° C. The IR and NMR spectra of this product agreed with those of a sample produced by the previously known method of synthesis.

Example 2

In 5 ml of 1,2-dichloroethane, 2.7 g of aluminium chloride was suspended. To the resultant suspension, 1.6 g (10 mmols) of succinyl chloride and 1.7 g (10 mmols) of 1-cyclooctenyl acetate were added at room temperature. The resultant mixture was stirred at 70° C. for five hours. The resultant mixture was poured into 50 ml of 1N hydrochloric acid containing ice and extracted three times with 30 ml of ethyl acetate. The aqueous layer that was extracted from the ethyl acetate layer twice with 30 ml of a saturated aqueous sodium bicarbonate solution was washed with ethyl acetate, adjusted to pH 1 to 2, again extracted three times with 30 ml of ethyl acetate. The organic layer was dried and concentrated. The residue was washed with water to give 0.2 g (9% in yield) of 7-(2,5-dioxocyclopentyl)heptanoic acid. It had a melting point of 135° to 146° C.

Example 3

To a suspension of 2.5 g of aluminium chloride in 10 ml of 1,2-dichloroethane, 1 g of succinic anhydride was added. The reaction mixture was stirred at room temperature for one and a half hour. To the mixture, 1.7 g of 1-cyclooctenyl acetate was added under cooling with ice over a period of three minutes. The resultant mixture was stirred at room temperature for 10 minutes. Then the mixture was refluxed for four hours, cooled, and poured into 50 ml of 1N hydrochloric acid containing ice. The reaction mixture was extracted four times with 30 ml of ethyl acetate. The organic layer was extracted with 30 ml of a saturated aqueous sodium bicarbonate solution. The extract was washed three times with 20 ml of ethyl acetate at pH 7. The aqueous layer was adjusted to pH 2 with 6N hydrochloric acid and extracted four times with 30 ml of ethyl acetate. The extract was dried and concentrated. The residue was washed with water to give 0.2 g of 7-(2,5-dioxocyclopentyl)heptanoic acid having a melting point of 110° to 125° C. The IR and NMR spectra of this compound agreed with those of an authentic sample.

EXAMPLE 4

To a solution of 2.7 g of aluminium chloride in 15 ml of nitromethane, 1.0 g of succinic anhydride was added, and then 1.7 g of 1-cyclooctenyl acetate was added dropwise under cooling. The resultant mixture was stirred at room temperature overnight and refluxed with stirring for four hours. The mixture was cooled, poured into 50 ml of 1N hydrochloric acid containing ice, and extracted four times with 30 ml of ethyl acetate. The organic layer was extracted twice with 30 ml of a saturated aqueous sodium bicarbonate solution. The aqueous layer was washed with ethyl acetate at pH 7. The aqueous layer was adjusted to pH 2 with 6N hydrochloric acid, and again extracted four times with 30 ml of ethyl acetate. The extract was dried and concentrated. The residue was washed with water to give 0.2 g of 7-(2,5-dioxocyclopentyl)heptanoic acid. This product had a melting point of 105° to 122° C.

Example 5

To a solution of 42 g (0.38 mol) of chlorotrimethylsilane and 78 g of triethylamine in 100 ml of dimethylformamide, a solution of 32 g (0.254 mol) of cyclooctanone in 40 ml of dimethylformamide was added. The resultant mixture was stirred at 100° to 115° C. for 48 hours. At the end of the reaction, the reaction mixture was combined with 240 ml of n-hexane and washed twice with 300 ml of a saturated aqueous sodium bicarbonate solution. The mixture was washed under cooling with 180 ml of 1.5N hydrochloric acid, then washed sequentially with an aqueous sodium bicarbonate solution, water, and saline and then dried with magnesium sulfate. The mixture was concentrated and distilled under a vacuum, to afford 40 g (80% in yield) of 1-cyclooctenyloxytrimethylsilane having a boiling point of 82° to 84° C./5 mmHg.

To a suspension of 2.6 g of aluminium chloride in 7 ml of 1,2-dichloroethane, 1 g (10 mmol) of succinic anhydride was added, and stirred at room temperature for one hour. To the resultant mixture, 2 g (10 mmol) of 1-cyclooctenyloxytrimethylsilane obtained as described above was added over a period of three minutes. The reaction mixture was stirred at room temperature for one hour and heated for 24 hours at 80° C. The resultant reaction mixture was cooled, poured into 50 ml of 1N hydrochloric acid containing ice, and extracted five times with 30 ml of ethyl acetate. The organic layer was extracted with 40 ml of a saturated aqueous sodium bicarbonate solution. The mixture was washed once with 20 ml of ethyl acetate at pH 7. The aqueous layer was adjusted to pH 1.5 with 6N hydrochloric acid and extracted three times with 30 ml of ethyl acetate. The extract was concentrated and the residue was washed with 3 ml of water. Consequently, 0.2 g (9% in yield) of 7-(2,5-dioxocyclopentyl)heptanoic acid having a melting point of 131° to 141° C. was obtained.

The IR and NMR spectra of this compound agreed with those of an authentic sample.

Example 6

To a suspension of 2.6 g (20 mmol) of aluminium chloride in 15 ml of 1,2-dichloroethane, 1 g (10 mmol) of succinic anhydride was added. The reaction mixture was stirred at room temperature for one hour. To the resultant mixture, 1.7 g (10 mmol) of 1-cyclooctenyl acetate was added under cooling with ice. The reaction mixture was stirred at room temperature for 10 minutes and then heated at 80° C. for 28 hours. The reaction mixture was cooled and poured into 50 ml of 1.5N hydrochloric acid containing ice. The reaction mixture was extracted four times with 30 ml of ethyl acetate. The organic layer was extracted with 40 ml of a saturated aqueous sodium bicarbonate solution. The aqueous layer was adjusted to pH 1.5 with 6N hydrochloric acid and extracted four times with 30 ml of ethyl acetate. The organic layer was washed with 30 ml of saline. The resultant mixture was concentrated. The residue was washed with 5 ml of water to give 0.40 g (18% in yield) of 7-(2,5-dioxocyclopentyl)heptanoic acid having a melting point of 133° to 138° C. The IR and NMR spectra of this compound agreed with those of an authentic sample.

Example 7

To a suspension of 2.6 g of aluminium chloride in 10 ml of 1,2-dichloroethane, 1 g of succinic anhydride was added. The reaction mixture was stirred at room temperature for 1.5 hours. To the resultant mixture, 1.7 g of 1-cyclooctenyl acetate and 2.5 g of chlorotrimethylsilane were added in the order mentioned under cooling with ice. The resultant mixture was stirred at room temperature for 20 hours and heated at 80° C. for 28 hours. The reaction mixture was cooled and poured into 50 ml of 1.5N hydrochloric acid containing ice. The mixture was extracted four times with 30 ml of ethyl acetate. The organic layer was extracted with 50 ml of a saturated aqueous sodium bicarbonate solution and 30 ml of water sequentially in the order mentioned. The aqueous layer was adjusted to pH 1.5 with 6N hydrochloric acid and extracted four times with 30 ml of ethyl acetate. The organic layer was washed with 30 ml of saline and concentrated. The residue was washed with 5 ml of water. Consequently, 0.53 g (24% in yield) of 7-(2,5-dioxocyclopentyl)heptanoic acid having a melting point of 131° to 138° C. was obtained.

Example 8

To a suspension of 5.5 g of aluminium bromide in 10 ml of 1,2-dichloroethane, 1.1 g of succinic anhydride was added. The reaction mixture was stirred at room temperature for one hour. To the resultant mixture, 1.9 g of 1-cyclooctenyl acetate was added under cooling with ice. The resultant mixture was stirred at room temperature for 30 minutes and heated at 80° C. for 27 hours. The reaction mixture was cooled, poured into 1.5N hydrochloric acid containing ice, and extracted five times with 40 ml of ethyl acetate. The organic layer was extracted with 50 ml of a saturated aqueous sodium bicarbonate solution and 20 ml of water. The aqueous solution was adjusted to pH 1.5 and extracted four times with 40 ml of ethyl acetate. The organic layer was washed with 30 ml of saline and concentrated. The residue was washed with 5 ml of water to yield 0.44 g of 7-(2,5-dioxocyclopentyl)heptanoic acid having a melting point of 129° to 137° C. The IR and NMR spectra of this compound agreed with those of an authentic sample.

Example 9

To a solution of 4 g of titanium tetrachloride in 5 ml of 1,2-dichloroethane, 1.08 g of succinic anhydride was added at room temperature. The resultant mixture was stirred for 30 minutes. To the resultant mixture, 1.79 g of 1-cyclooctenyl acetate was added. The mixture was stirred at room temperature for 30 minutes, refluxed for 45 hours, cooled, and poured into 50 ml of 1N hydrochloric acid containing ice. The resultant mixture was extracted three times with 30 ml of ethyl acetate. The ethyl acetate layer was washed with water and saline. The organic layer was extracted twice with 30 ml of a saturated aqueous sodium bicarbonate solution. The aqueous layers were combined and washed twice with 30 ml of ethyl acetate at pH 7.05. The aqueous layer was adjusted to pH 1.5 and extracted five times with 30 ml of ethyl acetate. The extract was dried and concentrated to afford 262.7 mg of a solid. The solid was washed twice with 1 ml of water. Consequently, 0.04 g of 7-(2,5-dioxocyclopentyl)heptanoic acid having a melting point of 135° to 143° C. was obtained.

Example 10

To a suspension of 2.6 g of aluminium chloride in 7 ml of 1,1,2-trichloroethane, 1 g of succinic anhydride was added. The mixture was stirred at room temperature for one hour. To the resultant mixture, 1.7 g of 1-cyclooctenyl acetate was added at room temperature. The reaction mixture was stirred for one hour and refluxed for 24 hours. The reaction mixture was cooled, poured into 50 ml of 1.5N hydrochloric acid containing ice, and extracted five times with 40 ml of ethyl acetate. The organic layer was washed once with 30 ml of water and extracted with 30 ml of a saturated aqueous sodium bicarbonate solution and 20 ml of water. The aqueous layer was adjusted to pH 1.5 and extracted four times with 40 ml of ethyl acetate. The organic layer was washed with 30 ml of saline and concentrated. The residue was washed with 6 ml of water to give 0.36 g of 7-(2,5-dioxocyclopentyl)heptanoic acid having a melting point of 124° to 134° C. The IR and NMR spectra of this compound agreed with those of an authentic sample.

Example 11

To a suspension of 2.6 g of aluminium chloride in 6 ml of 1,1,2,2-tetrachloroethane, 1 g of succinic anhydride was added. The reaction mixture was stirred at room temperature for one hour. To the resultant mixture, 1.7 g of 1-cyclooctenyl acetate was added at room temperature. The mixture was stirred for 1.5 hours and then refluxed for 22 hours. The reaction mixture was cooled, poured into 50 ml of 1.5N hydrochloric acid containing ice, and extracted five times with 40 ml of ethyl acetate. The organic layer was washed once with 30 ml of water, and extracted with 40 ml of a saturated aqueous sodium bicarbonate solution and 20 ml of water. The aqueous layer was adjusted to pH 1 and extracted four times with 40 ml of ethyl acetate. The organic layer was washed with 30 ml of saline and concentrated. The residue was washed with 3 ml of water to give 0.27 g of 7-(2,5-dioxocyclopentyl)heptanoic acid having a melting point of 127° to 135° C.

Example 12

To a suspension of 2.66 g of aluminium chloride in 1.55 g of succinic chloride, 1.66 g of 1-cyclooctenyl acetate was added at 0° C. The resultant mixture was stirred at room temperature for 20 minutes and then at 80° C. for 18 hours. The resultant mixture was poured into 50 ml of 1N hydrochloric acid containing ice and extracted three times with 30 ml of ethyl acetate. The ethyl acetate layer was washed with water and saline, and then extracted three times with 30 ml of a saturated aqueous sodium bicarbonate solution. The aqueous layer was washed with ethyl acetate, adjusted to pH 1-2, and extracted six times with 30 ml of ethyl acetate. The extract was dried and concentrated, to afford 263.9 mg of a solid. The solid was washed twice with 1 ml of water. Consequently, 0.15 g (7% in yield) of 7-(2,5-dioxocyclopentyl)heptanoic acid having a melting point of 130° to 140° C. was obtained. The IR and NMR spectra of this compound agreed with those of an authentic sample.

Example 13

In the presence of 0.2 g of para-toluenesulfonic acid, 16.5 g (0.13 mol) of cyclooctanone and 16.5 g (0.15 mol) of trimethyl orthoformate were stirred at room temperature for four hours. The resultant mixture was heated at 100° C. for 14 hours. The vacuum distillation of the mixture gave 13.7 g (75% in yield) of 1-methoxycyclooctene having a boiling point of 83° to 88° C./27 mmHg.

To a suspension of 2.6 g of aluminium chloride in 6 ml of 1,2-dichloroethane, 1 g (10 mmol) of succinic anhydride was added. The resultant mixture was stirred at room temperature for one and a half hour. To the resultant mixture, 1.5 g (11 m mol) of 1-methoxycyclooctene obtained as described above was added with stirring. At 85° C., the reactant was heated for 63 hours. The reaction mixture was cooled, poured into 50 ml of ice water, and extracted twice with 50 ml of butanol. The butanol layer was washed three times with 30 ml of water, combined with 20 ml of water, and adjusted to pH 6.9 with stirring. The aqueous layer was washed twice with 20 ml of butanol and adjusted to pH 2.0. The aqueous layer was extracted twice with 30 ml of butanol. The butanol layer was washed twice with 20 ml of water and concentrated to afford 0.6 g of a solid. The solid was washed with 3 ml of water, to afford 0.38 g (17% in yield) of 7-(2,5-dioxocyclopentyl)heptanoic acid having a melting point of 145° to 151° C. The NMR spectrum of this compound agreed with that of an authentic sample.

Example 14

In the presence of 0.3 g of para-toluenesulfonic acid, 20 g (0.16 mol) of cyclooctanone and 27 g (0.18 mol) of ethyl orthoformate were stirred at room temperature overnight. The resultant mixture was heated at 100° C. for 15 hours and distilled under reduced pressure to give 10.9 g (45% in yield) of 1-ethoxycyclooctene having a boiling point of 97.5° to 98.5° C./25 mmHg.

| NMR (deuterated chloroform) spectrum | |
|---|---|
| δ: 4.39 (t, J=8Hz, 1H) | vinyl-hydrogen |
| 3.60 (quartet, J=7Hz, 2H) | —O—$\underline{CH_2}$CH$_3$ |
| 2.35–1.70 (m, 4H) | —CH$_2$— at allyl position |
| 1.60–1.30 (m, 8H) | —CH$_2$— × 4 |
| 1.25 (t, J=7Hz, 3H) | —O—CH$_2$$\underline{CH_3}$ |

To a suspension of 2.6 g of aluminium chloride in 10 ml of 1,2-dichloroethane, 1 g (10 mmol) of succinic anhydride was added. The mixture was stirred at room temperature for two hours. To the resultant mixture, 1.7 g (11 mmol) of 1-ethoxycyclooctene obtained as described above was added with cooling. The resultant mixture was stirred at room temperature for 10 minutes and heated at 85° C. for 69 hours. The reaction mixture was cooled, poured into 50 ml of ice water, and extracted twice with 50 ml of butanol. The organic layer was washed three times with 30 ml of water. The organic layer was combined with 20 ml of water and adjusted to pH 6.9 with 1N NaOH with stirring. The aqueous layer was washed twice with 20 ml of butanol and adjusted to pH 2.0. The aqueous layer was extracted twice with 30 ml of butanol. The butanol extract was washed twice with 20 ml of water and concentrated. Consequently, 0.39 g of a solid was obtained. This solid was washed with 2 ml of water, to afford 220 mg (10% in yield) of 7-(2,5-dioxocyclopentyl)heptanoic acid having a melting point of 143° to 148° C. The NMR spectrum and TLC's Rf value agreed with those of an authentic sample.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method for the manufacture of 7-(2,5-dioxocyclopentyl) heptanoic acid represented by the formula:

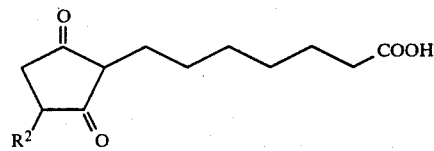

wherein R$^2$ stands for an acetyloxy group, a halogen atom, or a hydrogen atom, which comprises:
reacting a cyclooctene derivative represented by the formula

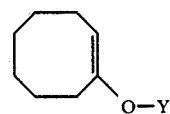

wherein Y stands for —R$^1$, —COR$^1$ or —SiR$^1$$_3$, wherein R$^1$ is an alkyl group of 1 to 5 carbon atoms or a benzyl group, with a compound represented by the formula

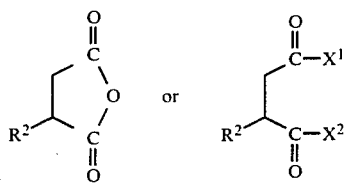

wherein $X^1$ and $X^2$ each is a halogen atom, in the presence of a Lewis acid.

2. The method of claim 1, wherein said reacting takes place in the presence of a halogenated trialkylsilane.

3. The method of claim 1, wherein said reacting takes place in the presence of a solvent selected from the group consisting of methylene chloride, 1,2-dichloroethane, nitromethane, nitrobenzene, 1,1,2-trichloroethane, and 1,1,2,2-tetrachloroethane.

4. The method of claim 1, which comprises reacting succinic anhydride with 1-cyclooctenyl acetate, succinyl chloride with 1-cyclooctenyl acetate, succinic anhydride with 1-cyclooctenyloxytrimethylsilane, succinic anhydride with 1-methoxycyclooctene, or succinic anhydride with 1-ethoxycyclooctene.

* * * * *